United States Patent
Francois

(10) Patent No.: US 7,049,299 B2
(45) Date of Patent: May 23, 2006

(54) METHOD FOR PREPARING TOOTHPASTE USING A SPECIFIC SORBITOL SYRUP, AND SORBITOL SYRUP

(75) Inventor: Alain Francois, Calonne sur la Lys (FR)

(73) Assignee: Roquette Freres, Lestrem (FR)

( * ) Notice: Subject to any disclaimer, the term of this patent is extended or adjusted under 35 U.S.C. 154(b) by 18 days.

(21) Appl. No.: 10/388,101

(22) Filed: Mar. 13, 2003

(65) Prior Publication Data

US 2003/0175219 A1 Sep. 18, 2003

Related U.S. Application Data

(63) Continuation of application No. PCT/FR02/02402, filed on Jul. 9, 2002.

(30) Foreign Application Priority Data

Jul. 18, 2001 (FR) .................................. 01 09609

(51) Int. Cl.
*A61K 8/00* (2006.01)
*A61K 31/70* (2006.01)
*C07H 1/00* (2006.01)

(52) U.S. Cl. .......................... 514/23; 426/658; 424/49; 424/401; 536/1.11

(58) Field of Classification Search ............ 424/49–58, 424/401; 536/104, 123.1, 123.13, 1.11; 568/852; 514/23; 426/658
See application file for complete search history.

(56) References Cited

U.S. PATENT DOCUMENTS

| | | | |
|---|---|---|---|
| 4,357,314 A | 11/1982 | Lynch | |
| 4,423,086 A * | 12/1983 | Devos et al. | ............... 427/2.18 |
| 5,252,313 A | 10/1993 | Collins et al. | |
| 5,773,604 A | 6/1998 | Lefevre et al. | |
| 6,417,346 B1 | 7/2002 | Salome et al. | |
| 6,528,069 B1 | 3/2003 | Lefevre et al. | |

FOREIGN PATENT DOCUMENTS

| WO | 95/22958 | 8/1995 |
|---|---|---|
| WO | 96/38123 | 12/1996 |

OTHER PUBLICATIONS

A partial Translation of "Pharmacopée Européenne"-2001, 0437, pp. 1456-1457.

* cited by examiner

*Primary Examiner*—Frederick Krass
(74) *Attorney, Agent, or Firm*—Young & Thompson

(57) ABSTRACT

The invention concerns a method for preparing toothpaste comprising a sorbitol syrup as main humectant, at least an abrasive and at least a gelling agent. The invention is characterized in that it consists in using as humectant, a sorbitol syrup with a dry matter content ranging between 73 and 82.9%, preferably between 74 and 80%.

3 Claims, No Drawings

METHOD FOR PREPARING TOOTHPASTE USING A SPECIFIC SORBITOL SYRUP, AND SORBITOL SYRUP

This application is a continuation of PCT/FR02/02402, filed Jul. 9, 2002.

The invention relates to a novel method for preparing toothpaste.

More precisely, the invention concerns a method for preparing toothpaste comprising a specific sorbitol syrup as main humectant.

Toothpastes are products well known in the state of the art. They generally comprise an abrasive agent and a gelling agent in a liquid medium consisting of a humectant and various ingredients such as flavors, colorants, preservatives, detergents, anti-tartar agents, antibacterial agents, and the like. These products are provided in the form of pastes, gels or liquids, which are opaque, translucent or transparent, and are used for cosmetic or therapeutic purposes.

The humectant most often consists of a polyol syrup such as sorbitol, glycerin, xylitol, mannitol and mixtures thereof. It is used to avoid hardening of toothpastes during storage and can also serve as sweetener.

Sorbitol is widely used in this application in the form of a noncrystallizable syrup, having a sorbitol content of about 70% on a dry basis, which is found on the market at 70% dry matter content, as in particular NEOSORB® 70/70 marketed by the applicant. In general, it is used in proportions of about 20 to 70% by weight of the toothpaste.

Numerous formulas comprising sorbitol containing 70% dry matter content have been described in particular in the documents U.S. Pat. No. 5,252,313, WO-A-95/22958, WO-A-96/38123.

One of the critical points in the preparation of a toothpaste relates to the dispersion of the gelling agent in the humectant. The gelling agent generally consists of polysaccharides such as celluloses or their derivatives, pectins, gelatins, agar, plant gums such as alginates, carrageenans, xanthans or inorganic gelling compounds such as thickening silicas, or polyacrylates. Although hydrophilic, the gelling agent tends to form lumps and to agglomerate. Some manufacturers circumvent the problem by being equipped with very high-shear mixers, but this equipment is very expensive. A solution to this problem was proposed in patent application EP-A-1,004,354 of which the applicant is proprietor, which describes polyol compositions whose dry matter content, of between 83 and 90%, was selected to ensure good dispersion of the gelling agents.

Toothpaste manufacturers are interested in the easy dispersion of gelling agents in these compositions and in the possibility of having more free water in order to be able to dissolve the active agents and the other ingredients of the toothpaste. However, they are hampered by the need to heat all the storage, handling and production materials in order to avoid risks of crystallization. Furthermore, during the preparation of toothpastes, the high viscosity of such compositions which results from the excellent dispersion of the gelling agent can prove too high for the stirring equipment in place.

Seeking to improve the state of the art, the applicant then observed that, within a specifically selected, very particular range of dry matter content, a sorbitol syrup offered the possibility of substantially improving the dispersion of abrasive agents in toothpaste and of advantageously reducing the production time of toothpastes, without exhibiting the disadvantages of sorbitol syrups of the prior art. The expression abrasive agents for the purposes of the present invention means compounds such as, for example, silicas or silica derivatives, calcium phosphates and calcium carbonate.

The present invention thus concerns a method for preparing toothpaste comprising a sorbitol syrup as main humectant, at least one abrasive agent and at least one gelling agent, characterized in that said sorbitol syrup has a dry matter content of between 73 and 82.9%, preferably between 74 and 80%.

The use of such a syrup for the preparation of toothpastes is novel. Its use in a method in accordance with the invention allows, surprisingly and unexpectedly, markedly improved dispersion of the abrasive agents, bringing about an advantageous gain in production time, and leads to stable and perfectly homogeneous products. Very good results in terms of gain in mixing time have been observed when silicas are for example used as abrasive agent. According to the invention, the toothpaste therefore preferably comprises, as abrasive agent, a compound chosen from the group consisting of silicas or silica derivatives, calcium carbonate and calcium phosphates. Still more preferably, said abrasive agent is a silica or a silica derivative.

Moreover, the use of the sorbitol syrup in accordance with the invention makes it possible, for the same final sorbitol concentration in the toothpaste, to have a larger quantity of free water to dissolve all the ingredients which it is desired to include in the paste. This results in a better homogeneity. The total water content of a toothpaste prepared according to the method in accordance with the invention is generally between 15 and 60% by weight, depending on the paste texture desired in the end.

A sorbitol syrup corresponding to the European Pharmacopoeia (2001 edition, 0437), namely a syrup comprising 72 to 92% dry weight of D-sorbitol, is preferably used in a method according to the invention. Advantageously, the sorbitol syrup in accordance with the invention is noncrystallizable.

In the present invention, said sorbitol syrup advantageously has a reducing sugar content of less than or equal to 500 ppm, preferably of less than 300 ppm, which makes it possible to use it in particular in toothpastes containing compounds of basic pH such as, for example, those which contain sodium bicarbonate, in which the syrup has excellent stability, that is to say an absence of coloration over time. This reducing sugar content may be determined by any technique known to persons skilled in the art and whose sensitivity is suited to relatively low contents. Advantageously, the test S, as described by the applicant in the documents EP-B1-0,711,743 or EP-A1-1,095,925, will be used.

To prepare the sorbitol syrup in accordance with the invention, it is possible to prepare a syrup from sorbitol powder by bringing it to the desired richness and dry matter content, or a commercial sorbitol may be directly concentrated to the desired dry matter content. This concentration is carried out using conventional evaporating devices.

It will be possible advantageously to use the sorbitol syrups as described in patent EP-B1-0,711,743 or obtained according to the method described in patent application EP-A1-1,095,925, which will be concentrated to the desired dry matter content.

According to another embodiment of the invention, the toothpaste may comprise an additional humectant such as, for example, glycerin, xylitol, propylene glycol, and polyethylene glycol. Preferably, the toothpaste comprises up to 20% by weight of said additional humectant.

As regards the preparation of the toothpaste, equipment and formulas known to persons skilled in the art will be used. According to a general embodiment of the method according to the invention, the humectant is first mixed with the gelling agent. This gelling agent is generally cellulose or a cellulose derivative such as, for example, carboxymethylcellulose. The various ingredients, such as flavors, sweeteners, colorants, fluorine salts, anti-tartar agents, antibacterial agents, whitening agents, detergents and preservatives are then added after homogenization.

The invention also concerns a sorbitol syrup, characterized in that it has a D-sorbitol content of between 72 and 92%, a dry matter content of between 73 and 82.9%, preferably between 74 and 80%, and a reducing sugar content of less than 500 ppm, preferably of less than 300 ppm. Preferably, said syrup has a total sugar content, after total hydrolysis according to the Bertrand method, of between 3.5 and 98%, preferably between 6 and 92%, and still more preferably between 8 and 90%. It may comprise, in addition, from 0.01 to 95% of hydrogenated mono- and/or disaccharides, the balance for 100 consisting of oligo- and polysaccharides. Still more preferably, said syrup is non-crystallizable.

The applicant has indeed observed that these syrups, which are particularly suited to good dispersion of the abrasive agents and other ingredients in a toothpaste, could be advantageously concentrated to the selected dry matter content without causing undesirable coloration, odors or tastes in the application targeted. Only the particular selection of such syrups leads to products which are stable, colorless and free of unpleasant tastes and odors, while the concentration of conventional sorbitol syrups is a delicate operation to perform because of the precautions to be taken in particular in terms of temperature.

The invention will be understood more clearly on reading the examples which follow, which are not intended to be limiting and which are only advantageous embodiments of the method in accordance with the invention.

EXAMPLE 1

Preparation of Toothpastes According to the Invention and Comparison with the Prior Art Various sorbitol syrups are prepared, as humectant, which have dry matter contents (DM) of 70% and 86.8% (prior art) and 74% and 78% (invention), by concentrating a sorbitol syrup (NEOSORB® 70/70). Various toothpastes, all containing the same sorbitol content, are prepared using these syrups.

The formula for each toothpaste is the following (percentages expressed by weight):

| | | |
|---|---|---|
| Silica (TIXOSIL 73): | | 14% |
| Silica (TIXOSIL 43): | | 9% |
| Detergent (SIPON LCSV95, 30% DM): | | 4.16% |
| Silesia mint flavor: | | 0.80% |
| Sodium monofluorophosphate: | | 0.76% |
| Carboxymethylcellulose (BLANOSE 7MXF): | | 0.7% |
| Green colorant (0.5% DM): | | 0.5% |
| Sodium saccharinate: | | 0.2% |
| Preservative (methylparaben): | | 0.18% |
| Preservative (propylparaben): | | 0.02% |
| Paste 1: | NEOSORB 70/70 containing 70% DM: | 64% |
| | Water: | 5.68% |
| Paste 2: | NEOSORB containing 74% DM: | 60.54% |
| | Water: | 9.14% |
| Paste 3: | NEOSORB containing 78% DM: | 57.44% |
| | Water: | 12.24% |
| Paste 4: | NEOSORB containing 86.8% DM: | 51.61% |
| | Water: | 18.07% |

Procedure:

Dissolve the parabens in water at 92° C. (solution S) in a beaker.

Mix the sorbitol syrup and the carboxymethylcellulose for 1 minute in a stainless steel bowl.

Add solution S, mix for 2 min.

Homogenize for 3 min.

Transfer into a GUEDU homogenizer (type 4.5NO) at 20° C.

Add the saccharinate, the monofluorophosphate, the colorant and the flavor, mix for 1 min 30 s under vacuum.

Add half of the silicas, mix for 3 min under vacuum.

Add the second half of the silicas, mix for 3 min under vacuum.

Mix for a time T until homogenization is obtained.

Add the SIPON, mix for 1 min 30 s under vacuum.

The total manufacturing time, the time T necessary for the dispersion of the silicas, the viscosity after manufacture and the viscosity after 24 hours (HELIPATH apparatus, viscosity in centipoises) are measured for each paste prepared.

The results are presented in the following table.

| | PASTE 1 | PASTE 2 | PASTE 3 | PASTE 4 |
|---|---|---|---|---|
| Total time | 30 min 30 s | 28 min 30 s | 21 min 30 s | — |
| Time T for mixing the silicas | 21 min 30 s | 19 min 30 s | 12 min 30 s | ** |
| Viscosity at T0 (cps) | 360 000 | 360 000 | 460 000 | |
| Viscosity at 24 h (cps) | 440 000 | 460 000 | 520 000 | |

**In this case, the incorporation of the second half of the silicas is incomplete because the viscosity of the mixture is too high for the mixer used.

Observations: The sorbitol syrups in accordance with the invention considerably reduce the time necessary for a perfectly homogeneous dispersion of the silicas. It is observed, according to the formulas according to the invention, that the quantity of available water is increased (up to 12% of water), which improves the dispersion and/or solubilization of the other ingredients. The viscosities are better, which causes an improved paste texture and a shorter silica mixing time.

In the case of paste 4, which is prepared with a sorbitol syrup containing 86.8% dry matter content, the dispersion of the silicas is insufficient.

The use of sorbitol syrups in accordance with the invention for the preparation of toothpastes is therefore technically and economically completely advantageous (large gain in time, improved paste quality). Such syrups are furthermore completely advantageous in terms of economics of cost of transportation, reduction in the volumes to be stored, and ease of use.

EXAMPLE 2

Formulation of Toothpastes with Calcium Carbonate

Toothpastes are prepared in accordance with example 1, replacing the abrasive silicas with calcium carbonate.

Sorbitol syrups (NEOSORB® 70/70) containing 70, 75 and 80% dry matter content (pastes 1, 2 and 3) are prepared. The sorbitol contents of each paste are identical.

The formula is the following:

| | | |
|---|---|---|
| Calcium carbonate (SOCAL 90A): | | 45% |
| Sipon LCSV95 (30% DM): | | 5.66% |
| Blanose 7MXF: | | 1.2% |
| Silesia mint flavor: | | 1% |
| Sodium monofluorophosphate: | | 0.8% |
| Sodium saccharinate: | | 0.2% |
| Methylparaben: | | 0.18% |
| Propylparaben: | | 0.02% |
| Paste 1: | NEOSORB 70/70 containing 70% DM: | 35.7% |
| | Water: | 10.29% |
| Paste 2: | NEOSORB containing 75% DM: | 33.32% |
| | Water: | 12.67% |
| Paste 3: | NEOSORB containing 80% DM: | 31.24% |
| | Water: | 14.75% |

Procedure:

Dissolve the parabens in water at 72° C. (solution S) in a beaker.

Mix the sorbitol syrup and the carboxymethylcellulose for 1 minute in a stainless steel bowl.

Add solution S, mix for 2 min.

Homogenize for 3 min.

Transfer into the GUEDU homogenizer at 20° C.

Add the saccharinate, the monofluorophosphate and the flavor, mix for 1 min 30 s under vacuum.

Add the carbonate, mix for 3 min under vacuum.

Add the Sipon, mix for 1 min 30 s under vacuum.

The total manufacturing time, and the time T necessary for the dispersion of the carbonate are measured for each paste prepared.

The results are presented in the following table:

| | PASTE 1 | PASTE 2 | PASTE 3 |
|---|---|---|---|
| Total manufacturing time | 15 min | 13 min 30 s | 12 min |
| Carbonate mixing time T | 6 min | 4 min 30 s | 3 min |

These results demonstrate that the abrasive mixing times are markedly improved when the sorbitol syrups in accordance with the invention are used.

The total toothpaste manufacturing time is thereby advantageously shortened.

EXAMPLE 3

Formulation of Toothpastes with Sodium Bicarbonate

Various sorbitol syrups are prepared, as humectant, which have dry matter contents (DM) of 70% (prior art) and 74%, 78% and 81.6% (invention), by concentrating a noncrystallizable sorbitol syrup having a reducing sugar content of less than 500 ppm, and a total sugar content of 7% after total hydrolysis according to the Bertrand method, and comprising 88% of hydrogenated mono- and/or disaccharides, the balance for 100 consisting of oligo- and polysaccharides (NEOSORB® 70/70 SB).

Various sodium bicarbonate toothpastes all containing the same dry sorbitol content (31.5%) were prepared using these syrups.

The formula for each toothpaste is the following (percentages expressed by weight):

| | |
|---|---|
| NEOSORB ® 70/70 SB: | 45.00% |
| Water: | 16.94% |
| Sodium bicarbonate: | 10.00% |
| Thickening silica Tixosil 43: | 10.00% |
| Abrasive silica Tixosil 73: | 9.00% |
| Sodium lauryl sulfate Sipon LCSV95 (30% DM): | 5.66% |
| Mint flavor: | 1.00% |
| Sodium monofluorophosphate: | 0.8% |
| Sodium carboxymethylcellulose Blanose 7MXF: | 0.7% |
| Titanium dioxide: | 0.7% |
| Sodium saccharinate: | 0.2% |

The procedure for each paste differs only in the application of an additional mixing time or not. This additional mixing time is intended for the possible removal of residual grains from the paste.

Procedure:

dissolve the monofluorophosphate and saccharinate in water in order to obtain a solution S, in a beaker;

mix the NEOSORB® and the CMC for 1 min (motor+turbine), in a stainless steel bowl;

add solution S and the titanium oxide, mix for 2 min;

homogenize for 3 min;

transfer to a GUEDU mixer;

add the flavor and mix under vacuum for 1 min 30 sec;

add the thickening silica and mix under vacuum for 3 min;

add the abrasive silica and mix under vacuum for 3 min;

add the bicarbonate and mix under vacuum for 3 min;

mix for an additional T min (according to the sorbitol syrup used);

add the Sipon and mix under vacuum for 1 min 30 sec.

The total manufacturing time, the additional time T necessary for the dispersion of the silicas, the viscosity after manufacture and the viscosity after cooling (HELIPATH apparatus, viscosity in centipoises), are measured for each paste prepared.

The results are presented in the table below:

| | | | | |
|---|---|---|---|---|
| Dry matter content of the sorbitol syrup (%) | 70 | 74 | 78 | 81.6 |
| Additional mixing time (min) | 9 | 6 | 3 | 0 |
| Total mixing time (min) | 27 | 24 | 21 | 18 |
| Paste viscosity after manufacture (cP) | 230 000 | 310 000 | 230 000 | 320 000 |
| Paste viscosity after cooling (cP) | 380 000 | 500 000 | 580 000 | 560 000 |

Comments: These results demonstrate, as in the preceding examples, that the sorbitol syrups in accordance with the invention advantageously allow a mixing time which is shorter, the higher the dry matter content, and allow better dispersion of the silicas, and perfect hydration of the carboxymethylcellulose, which results in a higher paste viscosity after manufacture.

What is claimed is:

1. A sorbitol syrup that is non-crystallizable at 20° C. and has a D-sorbitol content of between 72% and 77% by weight on a dry basis, a dry matter content of between 74 and 81.6%, and a reducing sugar content of less than 500 ppm.

2. The sorbitol syrup as claimed in claim 1, having a dry matter content of between 74 and 80%.

3. The sorbitol syrup as claimed in claim 1, having a reducing sugar content of less than 300 ppm.

* * * * *